US008529952B2

(12) United States Patent  
Criere et al.

(10) Patent No.: US 8,529,952 B2
(45) Date of Patent: *Sep. 10, 2013

(54) PHARMACEUTICAL COMPOSITION CONTAINING FENOFIBRATE AND METHOD FOR THE PREPARATION THEREOF

(75) Inventors: Bruno Criere, Gravigny (FR); Pascal Suplie, Montaure (FR); Philippe Chenevier, Montreal (CA); Pascal Oury, Le Chesnay (FR); Keith S. Rotenberg, Denville, NJ (US); George Bobotas, Tarpon Springs, FL (US)

(73) Assignee: Ethypharm, Saint-Cloud (FR)

( * ) Notice: Subject to any disclaimer, the term of this patent is extended or adjusted under 35 U.S.C. 154(b) by 508 days.

This patent is subject to a terminal disclaimer.

(21) Appl. No.: 12/686,574

(22) Filed: Jan. 13, 2010

(65) Prior Publication Data

US 2010/0112049 A1 May 6, 2010

Related U.S. Application Data

(63) Continuation of application No. 10/677,861, filed on Oct. 3, 2003, now Pat. No. 7,863,331, which is a continuation-in-part of application No. 10/030,262, filed as application No. PCT/FR00/01971 on Jul. 7, 2000, now Pat. No. 7,101,574.

(30) Foreign Application Priority Data

Jul. 9, 1999 (FR) ...................................... 99 08923

(51) Int. Cl.
*A61K 9/14* (2006.01)
*A61K 9/56* (2006.01)

(52) U.S. Cl.
USPC ............ 424/489; 424/456; 424/459; 424/462

(58) Field of Classification Search
USPC .................. 424/489, 456, 459, 462
See application file for complete search history.

(56) References Cited

U.S. PATENT DOCUMENTS

| | | | |
|---|---|---|---|
| 3,914,286 A | 10/1975 | Mieville | |
| 4,058,552 A | 11/1977 | Mieville | |
| 4,344,934 A | 8/1982 | Martin et al. | |
| 4,412,986 A | 11/1983 | Kawata et al. | |
| 4,717,569 A | 1/1988 | Harrison et al. | |
| 4,752,470 A | 6/1988 | Mehta | |
| 4,800,079 A | 1/1989 | Boyer et al. | |
| 4,895,726 A | 1/1990 | Curtet et al. | |
| 5,145,684 A | 9/1992 | Liversidge et al. | |
| 5,545,628 A | 8/1996 | Deboeck et al. | |
| 5,558,879 A | 9/1996 | Chen et al. | |
| 5,776,495 A | 7/1998 | Duclos et al. | |
| 5,840,330 A | 11/1998 | Stemmle et al. | |
| 6,074,670 A | 6/2000 | Stamm et al. | |
| 6,277,405 B1 | 8/2001 | Stamm et al. | |
| 6,368,620 B2 | 4/2002 | Liu et al. | |
| 6,423,517 B2 | 7/2002 | Becker et al. | |
| 6,667,064 B2 | 12/2003 | Surette | |
| 6,696,084 B2 | 2/2004 | Pace et al. | |
| 7,101,574 B1 | 9/2006 | Criere et al. | |
| 2004/0137055 A1 | 7/2004 | Criere et al. | |
| 2006/0083783 A1 | 4/2006 | Doyle et al. | |
| 2007/0071812 A1 | 3/2007 | Criere et al. | |
| 2007/0248101 A1 | 10/2007 | Zeitak | |

FOREIGN PATENT DOCUMENTS

| | | |
|---|---|---|
| EP | 012 523 B2 | 6/1980 |
| EP | 0164 959 A2 | 12/1985 |
| EP | 0 330 532 A1 | 8/1989 |
| EP | 0 514 967 A1 | 11/1992 |
| EP | 0 519 144 A1 | 12/1992 |
| EP | 793 958 A2 | 9/1997 |
| HU | 219 341 B | 3/1997 |
| WO | WO 82/01649 | 5/1982 |
| WO | WO 96/01621 A1 | 2/1996 |
| WO | WO 98/00116 A | 1/1998 |
| WO | WO 98/31360 | 7/1998 |
| WO | WO 98/31361 A | 7/1998 |
| WO | WO 98/31361 A1 | 7/1998 |
| WO | WO 01/03693 A1 | 1/2001 |

OTHER PUBLICATIONS

The Merck Index—An encyclopedia of chemicals, drugs and biologicals. Twelfth edition. 1996, p. 3260.
The Merck Index—An encyclopedia of chemicals, drugs and biologicals. Thirteenth edition. 2001, p. 3238.
International Search Report issued Oct. 26, 2000 in PCT/FR00/01971.
A. Munoz et al., "Micronised Fenofibrate", *Atherosclerosis* 110 (Suppl.) (1994) S45-S48, Elsevier Science, Ireland.
D.F. Temeljotov et al., "Solubilization and Dissolution Enhancement for Sparingly Soluble Fenofibrate", *Acta. Pharm.* 46 (1996) 131-136.
I. Ghebre-Sellassie "Pellets: A General Overview", Pharmaceutical Pelletization Technology, Drugs and the Pharmaceutical Sciences, 37, pp. 2, 3, 234, edited by Isaac Ghebre-Sellassie, Marcel Dekker, Inc. NY NY.
R. Bianchini et al., "Influence of Drug Loading on Coated Beads Release Using Air Suspension Technique", *Boll. Chim. Farmaceutico*, 128 Dec. 12, 1989, pp. 373-379.
Dr. Bernhard Luy, "Methods of Pellet Production", Presented at Glatt Symposium, Strasbourg, Oct. 1992, pp. 1-12, with curriculum vitae.
A. Kuchiki et al., "Stable Solid Dispersion System Against Humidity", *Yakuzaigaku* 44(1) 31-37 (1984) pp. 1-13.
JP Guichard et al., "A New Formulation of Fenofibrate: Suprabioavailable Tablets", *Current Medical Research and Opinion* 16(2) (2000) pp. 134-138, Laboratoires Fournier, France.
El-Arini et al. "Dissolution Properties of Praziquantel-PVP systems," *Pharmaceutical Acta Helvetiae* v. 72, pp. 89-94 (1998).
U.S. Department of Health and human Services Food and Drug Administration Center for Drug Evaluation and Research 9CDER) Oct. 1997 pp. 1-8.
cancerweb.ncl.ac.uk/cgi-bin/omd?inert 1997, 1 page.
"TriCor, Micronized Fenofibrate, Now Available in U.S. for High Triglycerides" 2 pages, Jun. 2, 1998 http://www.pslgroup.com/dg/81D66.htm.

*Primary Examiner* — Shirley V Gembeh
(74) *Attorney, Agent, or Firm* — RatnerPrestia (57) ABSTRACT

Pharmaceutical compositions comprising micronized fenofibrate, a surfactant and a binding cellulose derivative as a solubilization adjuvant, wherein said compositions contain an amount of fenofibrate greater than or equal to 60% by weight and methods of producing fenofibrate compositions.

34 Claims, 5 Drawing Sheets

PHARMACEUTICAL COMPOSITION CONTAINING FENOFIBRATE AND METHOD FOR THE PREPARATION THEREOF

RELATED APPLICATIONS

This application is a continuation of U.S. Ser. No. 10/677,861, filed Oct. 3, 2003, which is a continuation in part of U.S. Ser. No. 10/030,262, filed Apr. 17, 2002, which is a 371 of PCT/FR00/01971 filed on Jul. 7, 2000.

FIELD OF THE INVENTION

The present invention relates to a novel pharmaceutical composition containing fenofibrate.

1. Background of the Invention

Fenofibrate is recommended in the treatment of adult endogenous hyperlipidemias, of hypercholesterolemias and of hypertriglyceridemias. A treatment of 300 to 400 mg of fenofibrate per day enables a 20 to 25% reduction of cholesterolemia and a 40 to 50% reduction of triglyceridemia to be obtained.

The major fenofibrate metabolite in the plasma is fenofibric acid. The half-life for elimination of fenofibric acid from the plasma is of the order of 20 hours. Its maximum concentration in the plasma is attained, on average, five hours after ingestion of the medicinal product. The mean concentration in the plasma is of the order of 15 micrograms/ml for a dose of 300 mg of fenofibrate per day. This level is stable throughout treatment.

Fenofibrate is an active principle which is very poorly soluble in water, and the absorption of which in the digestive tract is limited.

Due to its poor affinity for water and to its hydrophobic nature, fenofibrate is much better absorbed after ingestion of food, than in fasting conditions. This phenomenon called "food effect" is particularly important when comparing fenofibrate absorption in high fat meal conditions versus fasting conditions.

The main drawback in this food effect is that food regimen must be controlled by the patient who is treated with fenofibrate, thereby complicating the compliance of the treatment. Yet, as fenofibrate is better absorbed in high fat meal conditions, it is usually taken after a fat meal. Therefore, these conditions of treatment are not adapted to patients treated for hyperlipidemia or hypercholesterolemia who must observe a low fat regimen.

A way to limit the food effect is to increase the solubility or the rate of solubilization of fenofibrate, thereby leading to a better digestive absorption, whichever the food regimen.

2. Description of the Related Art

Various approaches have been explored in order to increase the rate of solubilization of fenofibrate: micronization of the active principle, addition of a surfactant, and comicronization of fenofibrate with a surfactant.

Patent EP 256 933 describes fenofibrate granules in which the fenofibrate is micronized in order to increase its bioavailability. The crystalline fenofibrate microparticles are less than 50 μm in size. The binder used is polyvinylpyrrolidone. The document suggests other types of binder, such as methacrylic polymers, cellulose derivatives and polyethylene glycols. The granules described in the examples of EP 256 933 are obtained by a method using organic solvents.

Patent EP 330 532 proposes improving the bioavailability of fenofibrate by comicronizing it with a surfactant, such as sodium lauryl sulfate. The comicronizate is then granulated by wet granulation in order to improve the flow capacities of the powder and to facilitate the transformation into gelatin capsules. This comicronization allows a significant increase in the bioavailability compared to the use of fenofibrate described in EP 256 933. The granules described in EP 330 532 contain polyvinylpyrrolidone as a binder.

This patent teaches that the comicronization of fenofibrate with a solid surfactant significantly improves the bioavailability of the fenofibrate compared to the use of a surfactant, of micronization or of the combination of a surfactant and of micronized fenofibrate.

Patent WO 98/31361 proposes improving the bioavailability of the fenofibrate by attaching to a hydrodispersible inert support micronized fenofibrate, a hydrophilic polymer and, optionally, a surfactant. The hydrophilic polymer, identified as polyvinylpyrrolidone, represents at least 20% by weight of the composition described above.

This method makes it possible to increase the rate of dissolution of the fenofibrate, and also its bioavailability. However, the preparation method according to that patent is not entirely satisfactory since it requires the use of a considerable amount of PVP and of the other excipients. The example presented in that patent application refers to a composition containing only 17.7% of fenofibrate expressed as a mass ratio. This low mass ratio for fenofibrate leads to a final form which is very large in size, hence a difficulty in administering the desired dose of fenofibrate, or the administration of two tablets.

DETAILED DESCRIPTION OF THE INVENTION

In the context of the present invention, it has been discovered that the incorporation of a cellulose derivative, used as a binder and solubilization adjuvant, into a composition containing micronized fenofibrate and a surfactant makes it possible to obtain a bioavailability which is greater than for a composition containing a comicronizate of fenofibrate and of a surfactant. It has further been discovered the pharmaceutical composition of the present invention makes it possible to obtain comparable bioavailability to prior art formulations containing a higher dosage of micronized fenofibrate.

More particularly, it has been observed that bioavailability of fenofibrate is increased when microgranules according to the present invention are prepared by mixing together in a liquid phase the fenofibrate, the surfactant and the binding cellulose derivative before spraying this liquid phase onto neutral cores.

Indeed, both cellulose derivative and surfactant are dissolved in the liquid phase in which the microparticles of micronized fenofibrate are in suspension.

Thus, when the solvent is removed from the suspension by evaporation after spraying onto neutral cores, molecules of both cellulose derivative and surfactant are adsorbed directly onto the fenofibrate microparticles. This phenomenon induces a very homogeneous reparation and creates a very close contact between fenofibrate microparticles and these molecules, which are responsible for its better solubilization in the gastro-intestinal fluids and thereby allow a better absorption of fenofibrate, also contributing to a reduction of the food effect as mentioned above.

Thus, it has been discovered that the pharmaceutical composition of the present invention has less food effect than prior art formulations when administered to patient, i.e. the inventive formulation is less dependent on the presence of food in the patient to achieve high bioavailability. For example, prior art fenofibrate formulations must be taken with food to achieve high bioavailability. The inventors have unexpectedly discovered a fenofibrate composition that achieves high bioavailability almost independent of the presence of food in a patient.

Finally, it has been discovered that the addition of an outer layer of a hydrosoluble binder results in a novel in vivo profile, with the following limits: less than 10% in 5 minutes and more than 80% in 20 minutes, as measured using the rotating blade method at 75 rpm according to the European Pharmacopoeia, in a dissolution medium constituted by water with 2% by weight polysorbate 80 or in a dissolution medium constituted by water with 0.025M sodium lauryl sulfate.

A subject of the present invention is therefore a pharmaceutical composition containing micronized fenofibrate, a surfactant and a binding cellulose derivative, that become intimately associated after the removing of the solvent used in the liquid phase.

The composition of the invention is advantageously provided as gelatin capsules containing granules. These granules may in particular be prepared by assembly on neutral cores, by spraying an aqueous solution containing the surfactant, the solubilized binding cellulose derivative and the micronized fenofibrate in suspension.

For example, the pharmaceutical composition of the present invention may include a composition in the form of granules comprising:
  (a) a neutral core; and
  (b) an active layer, which surrounds the neutral core;
wherein said neutral core may include lactose, mannitol, a mixture of sucrose and starch or any other acceptable sugar, and wherein said active layer comprises the micronized fenofibrate, the surfactant and the binding cellulose derivative.

Or, for example, the pharmaceutical composition of the present invention may include an immediate release fenofibrate composition including (a) a neutral core; (b) an active layer, which surrounds the core; and (c) an outer layer; wherein the active layer comprises micronized fenofibrate, a surfactant and a binding cellulose derivative.

The pharmaceutical composition according to the present invention has a high proportion of fenofibrate; it may therefore be provided in a formulation which is smaller in size than the formulations of the prior art, which makes this composition according to the invention easy to administer. Further, the pharmaceutical composition of the present invention provides comparable bioavailability to prior art formulations at higher dosage strengths of fenofibrate. Thus, the inventive composition provides advantages over prior art formulations. For example, the inventive formulation containing only 130 mg of fenofibrate has comparable bioavailability with a prior art formulation containing 200 mg of fenofibrate under fed or fasted conditions, and with single or multiple dosing.

The amount of fenofibrate is greater than or equal to 60% by weight, preferably greater than or equal to 70% by weight, even more preferably greater than or equal to 75% by weight, relative to the weight of the composition.

In the context of the present invention, the fenofibrate is not comicronized with a surfactant. On the contrary, it is micronized alone and then combined with a surfactant and with the binding cellulose derivative, which is a solubilization adjuvant.

The surfactant is chosen from surfactants which are solid or liquid at room temperature, for example sodium lauryl sulfate, Polysorbate® 80 (polyoxyethylene 20 sorbitan monooleate), Montane® 20 or sucrose stearate, preferably sodium lauryl sulfate.

The fenofibrate/HPMC ratio is preferably between 5/1 and 15/1.

The surfactant represents between about 1 and 10%, preferably between about 3 and 5%, by weight relative to the weight of fenofibrate.

The binding cellulose derivative represents between about 2 and 20%, preferably between 5 and 12%, by weight of the composition.

Hydroxypropylmethylcellulose is preferably chosen, the apparent viscosity of which is between 2.4 and 18 cP, and even more preferably between about 2.4 and 3.6 cP, such as for example Pharmacoat 603®.

The mean size of the fenofibrate particles is less than 15 preferably 10 even more preferably less than 8 µm.

The composition of the invention may also contain at least one excipient such as diluents, for instance lactose, antifoaming agents, for instance Dimethicone® ($\alpha$-(trimethylsilyl)-$\gamma$-methylpoly[oxy(dimethylsilylene)]) and Simethicone® (mixture of $\alpha$-(trimethylsilyl)-$\gamma$-methylpoly[oxy(dimethylsilylene)] with silicon dioxide), or lubricants, for instance talc or colloidal silicon dioxide such as Aerosil®.

The antifoaming agent may represent between about 0 and 10%, preferably between about 0.01 and 5%, even more preferably between about 0.1 and 0.7%, by weight of the composition.

The lubricant may represent between about 0 and 10%, preferably between about 0.1 and 5%, even more preferably between about 0.2 and 0.6%, by weight of the composition.

The composition of the invention may also include a outer coating or layer of a hydrosoluble binder. The hydrosoluble binder of the outer layer represents between about 1 and 15%, preferably between about 1 and 8%, even more preferably between about 2-4% by weight of the composition. The hydrosoluble binder may include hydroxypropylmethylcellulose, polyvinylpyrrolidone, or hydroxypropylcellulose or a mixture thereof. However, one of ordinary skill in the art would understand other substances that may be used as the hydrosoluble binder in the outer layer.

Hydroxypropylmethylcellulose is preferably chosen, the apparent viscosity of which is between 3 and 15 cP, such as for example Pharmacoat 606®, or a mixture of different grades varying in viscosity. The amount of HPMC in the outer layer is inversely proportional to viscosity. It is within the skill in the art to determine the amount of hydrosoluble binder to obtain the claimed properties in the dissolution profile.

The outer layer may also include one or more excipient such as lubricants, for instance talc. The lubricant may represent between about 0 and 10%, preferably between about 1 and 5%, even more preferably between about 1-2%, by weight of the composition.

The pharmaceutical composition of the invention advantageously consists of granules in an amount equivalent to a dose of fenofibrate of between 50 and 300 mg, preferably between 130 and 200 mg and more preferably equal to 200 mg.

These granules preferably comprise:
  (a) a neutral core;
  (b) an active layer, which surrounds the core; and
  (c) an outer layer.

The expression "outer layer" means an outer coating which is applied on the neutral core (A) coated with the active layer (B). Said coating may consist of one or several layers.

The outer layer may comprise a hydrosoluble binder.

The hydrosoluble binder of the outer layer may include hydroxypropylmethylcellulose, polyvinylpyrrolidone, or hydroxypropylcellulose. However, one of ordinary skill in the art would understand other substances that may be used as the binding cellulose derivative in the outer layer.

In the outer layer, hydroxypropylmethylcellulose is preferably chosen among Hydroxypropylmethylcellulose having an apparent viscosity of 3 cP, such as Pharmacoat 603®, or 6 cP, such as Pharmacoat 606®, or 15 cP such as Pharmacoat 615®.

The outer layer may further comprise talc. In that case, the HPMC/talc mass ratio is preferably comprised between 1/1 and 5/1.

The present invention also relates to a pharmaceutical composition of fenofibrate that can be administered to provide substantial reduction of an effect of food on the uptake of the fenofibrate, i.e. substantial reduction of the food effect.

Such a pharmaceutical composition presents the advantage of being almost independent of the food conditions. Such a composition substantially reduces or eliminates the difference of bioavailability observed in function of the nature of the meal and between fed and fasted conditions.

Indeed, food can change the bioavailability of a drug, which can have clinically significant consequences. Food can alter bioavailability by various means, including: delaying gastric emptying, stimulating bile flow, changing gastrointestinal (GI) pH, increasing splanchnic blood flow, changing luminal metabolism of a drug substance, and physically or chemically interacting with a dosage form or a drug substance. Food effects on bioavailability are generally greatest when the drug product is administered shortly after a meal is ingested, such as provided in prior art fenofibrate formulations. The nutrient and caloric contents of the meal, the meal volume, and the meal temperature can cause physiological changes in the GI tract in a way that affects drug product transit time, luminal dissolution, drug permeability, and systemic availability. In general, meals that are high in total calories and fat content are more likely to affect the GI physiology and thereby result in a larger effect on the bioavailability of a drug substance or drug product. Notably, fenofibrate is prescribed for cholesterol management to patients who cannot eat high fat foods. Thus, there is a need for a fenofibrate composition that need not be administered with high fat foods. The present invention, unlike prior art fenofibrate formulation, achieves high bioavailability irrespective of the presence of food.

Accordingly, a method of reducing food effect is provided when treating hyperlipidemias, hypercholesterolemias and hypertriglyceridemias in a patient, including the steps of administering to the patient an effective amount of the instant invention. Further, the bioavailability of the composition is equivalent whether the patient is fed a high fat meal, a therapeutic lifestyle change diet, or when the patient is fasted.

In addition, the invention provides a composition comprising fenofibrate having a novel in vivo dissolution profile of less than 10% in 5 minutes and more than 80% in 20 minutes, as measured using the rotating blade method at 75 rpm according to the European Pharmacopoeia, in a dissolution medium constituted by water with 2% by weight polysorbate 80 or in a dissolution medium constituted by water with 0.025M sodium lauryl sulfate.

The composition according to the present invention, advantageously has a dissolution profile less than 5% at 5 minutes and more than 90% at 20 minutes, as measured using the rotating blade method at 75rpm according to the European Pharmacopeia in a dissolution medium constituted by water with 0.25M sodium lauryl sulfate.

The present invention also relates to a method for preparing the granules, the composition of which is described above. This method uses no organic solvent.

The granules are prepared by assembly on neutral cores.

The neutral cores have a particle size of between 200 and 1000 microns, preferably between 400 and 600 microns. The neutral cores may represent between about 1 and 50%, preferably between about 10 and 20%, even more preferably between about 14-18%, by weight of the composition.

The assembly is carried out in a sugar-coating pan, in a perforated coating pan or in a fluidized airbed, preferably in a fluidized airbed.

The assembly on neutral cores is carried out by spraying an aqueous solution containing the surfactant, the solubilized binding cellulose derivative, and the micronized fenofibrate in suspension, and then optionally, by spraying an aqueous solution containing the the hydrosoluble binder.

The invention is illustrated in a non limiting way by the following examples

EXAMPLES

Although the present invention has been described in detail with reference to examples above, it is understood that various modifications can be made without departing from the spirit of the invention, and would be readily known to the skilled artisan. Additionally, the invention is not to be construed to be limited by the following examples.

Example 1

Granules

1A) Microgranules (XFEN 1735)

The microgranules are obtained by spraying an aqueous suspension of micronized fenofibrate onto neutral cores. The composition is given in the following table:

| Formula | Amount (percentage by mass) |
| --- | --- |
| Micronized fenofibrate | 64.5 |
| Neutral cores | 21 |
| HPMC (Pharmacoat 603 ®) | 11.2 |
| Polysorbate ® 80 | 3.3 |
| Fenofibrate content | 645 mg/g |

The in vitro dissolution was determined according to a continuous flow cell method with a flow rate of 8 ml/min of sodium lauryl sulfate at. 0.1 N. The percentages of dissolved product as a function of time, in comparison with a formulation of the prior art, Lipanthyl 200 M, are given in the following table.

|  | Time (min) | |
|---|---|---|
|  | 15 | 30 |
| Example 1A (% dissolved) | 73 | 95 |
| Lipanthyl 200M (% dissolved) | 47.3 | 64.7 |

Formulation 1A dissolves more rapidly than Lipanthyl 200 M.

1B) Microgranules (X FEN 1935)

The mean size of the fenofibrate particles is equal to 6.9±0.7 microns.

The microgranules are obtained by spraying an aqueous suspension onto neutral cores. The suspension contains micronized fenofibrate, sodium lauryl sulfate and HPMC. The assembly is carried out in a Huttlin fluidized airbed (rotoprocess).

The formula obtained is given below.

| FORMULA | AMOUNT (percentage by mass) |
|---|---|
| Micronized fenofibrate | 65.2 |
| Neutral cores | 20.1 |
| HPMC (Pharmacoat 603 ®) | 11.4 |
| Sodium lauryl sulfate | 3.3 |
| Fenofibrate content | 652 mg/g |

The size of the neutral cores is between 400 and 600 µm.

1C) Gelatin Capsules of Microgranules (Y FEN 001)

Microgranules having the following composition are prepared:

| RAW MATERIALS | AMOUNT (percentage by mass) |
|---|---|
| Micronized fenofibrate | 67.1 |
| Neutral cores | 17.2 |
| Pharmacoat 603 ® (HPMC) | 11.7 |
| Sodium lauryl sulfate | 3.3 |
| 35% dimethicone emulsion | 0.2 |
| Talc | 0.5 |
| Fenofibrate content | 671 mg/g | according to the method described in paragraph 1A).

The microgranules obtained are distributed into size 1 gelatin capsules, each containing 200 mg of fenofibrate.

The in vitro dissolution is determined according continuous flow cell method with a flow rate of 8 ml/min of sodium lauryl sulfate at 0.1 N. The comparative results with a formulation of the prior art, Lipanthyl 200 M, are given in the following table.

|  | Time (min) | |
|---|---|---|
|  | 15 | 30 |
| Example 1C (% dissolved) | 76 | 100 |
| Lipanthyl 200M (% dissolved) | 47.3 | 64.7 |

Formula 1C dissolves more rapidly than Lipanthyl 200 M.

The gelatin capsules are conserved for 6 months at 40° C./75% relative humidity. The granules are stable under these accelerated storage conditions. In vitro dissolution tests (in continuous flow cells with a flow rate of 8 ml/min of sodium lauryl sulfate at 0.1 N) were carried out. The percentages of dissolved product as a function of time for gelatin capsules conserved for 1, 3 and 6 months are given in the following table.

| Dissolution time (min) | Conservation time | | |
|---|---|---|---|
|  | 1 month (% dissolved product) | 3 months (% dissolved product) | 6 months (% dissolved product) |
| 5 | 25.1 | 23.0 | 20.1 |
| 15 | 71.8 | 65.6 | 66.5 |
| 25 | 95.7 | 88.7 | 91.0 |
| 35 | 104.7 | 98.7 | 98.2 |
| 45 | 106.4 | 100.2 | 99.1 |
| 55 | 106.7 | 100.5 | 99.5 |
| 65 | 106.8 | 100.6 | 99.7 |

The evolution of the content of active principle during storage is given in the following table.

|  | Conservation time | | | |
|---|---|---|---|---|
|  | 0 | 1 month | 3 months | 6 months |
| Content (mg/gelatin Capsule) | 208.6 | 192.6 | 190.8 | 211.7 |

Pharmacokinetic Study Carried Out in Fasting Individuals

The in vivo release profile of the gelatin capsules containing the example 1 C granules at a dose of 200 mg of fenofibrate is compared with that of the gelatin capsules marketed under the trademark Lipanthyl 200 M.

This study is carried out in 9 individuals. Blood samples are taken at regular time intervals and fenofibric acid is assayed.

The results are given in the following table and FIG. 1.

| Pharmacokinetic parameters | Lipanthyl 200M | Example 1C |
|---|---|---|
| $AUC_{o-t}$ (µg · h/ml) | 76 | 119 |
| $AUC_{inf}$ (µg · h/ml) | 96 | 137 |
| $C_{max}$ (µg/ml) | 2.35 | 4.71 |
| $T_{max}$ (hours) | 8.0 | 5.5 |
| Ke (1/hour) | 0.032 | 0.028 |
| Elim ½ (hours) | 26.7 | 24.9 |

The following abbreviations are used in the present application:

| | |
|---|---|
| $C_{max}$: | maximum concentration in the plasma, |
| $T_{max}$: | time required to attain the $C_{max}$, |
| Elim ½: | plasmatic half-life, |
| $AUC_{0-t}$: | area under the curve from 0 to t, |
| $AUC_{0-\infty}$: | area under the curve from 0 to ∞, |
| Ke: | Elimination constant. |

Figure 1:
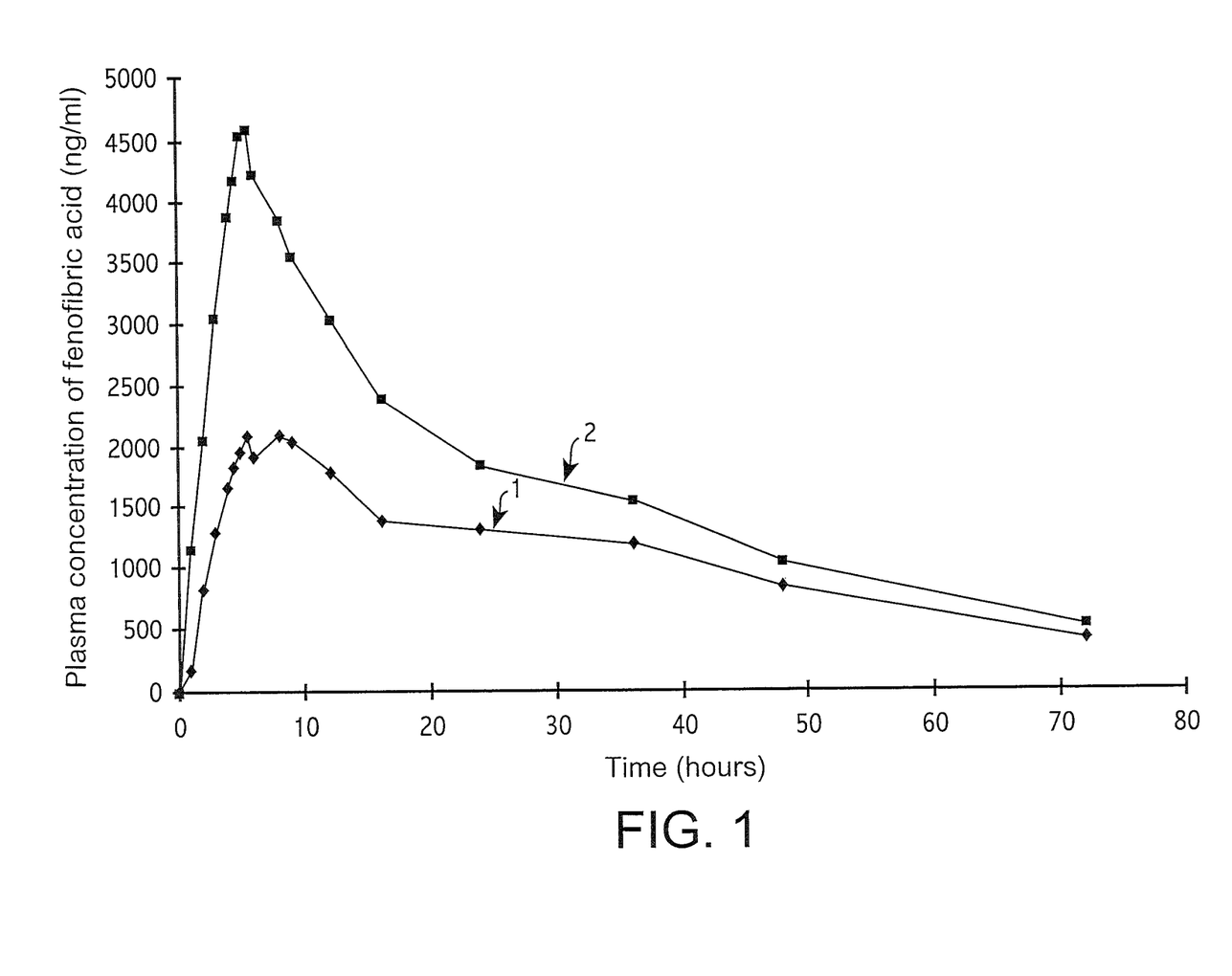
FIG. 1 represents the in vivo release profile of the formulation of example 1C and of a formulation of the prior art in fasting individuals. (Curve 1: Lipanthyl® 200M Curve 2; composition according to the present invention).

The results obtained for Lipanthyl 200 M and for the product of example 1C are represented on FIG. 1 by curves 1 and 2, respectively.

These results show that the composition according to the present invention has a bioavailability which is greater than that of Lipanthyl 200 M in fasting individuals.

Pharmacokinetic Study Carried Out in Individuals in Fed Condition

The in vivo release profile of the gelatin capsules containing the example 1 C granules at a dose of 200 mg of fenofibrate is compared with that of the gelatin capsules marketed under the trademark Lipanthyl 200 M.

This study is carried out in 18 individuals. Blood samples are taken at regular time intervals and fenofibric acid is assayed.

The results are given in the following table and FIG. 2.

| Pharmacokinetic parameters | Lipanthyl 200M | Example 1C |
|---|---|---|
| $AUC_{o-t}$ (µg · h/ml) | 244 | 257 |
| $AUC_{inf}$ (µg · h/ml) | 255 | 270 |
| $C_{max}$ (µg/ml) | 12 | 13 |
| $T_{max}$ (hours) | 5.5 | 5.5 |
| Ke (1/hour) | 0.04 | 0.04 |
| Elim ½ (hours) | 19.6 | 19.3 |

Figure 2:
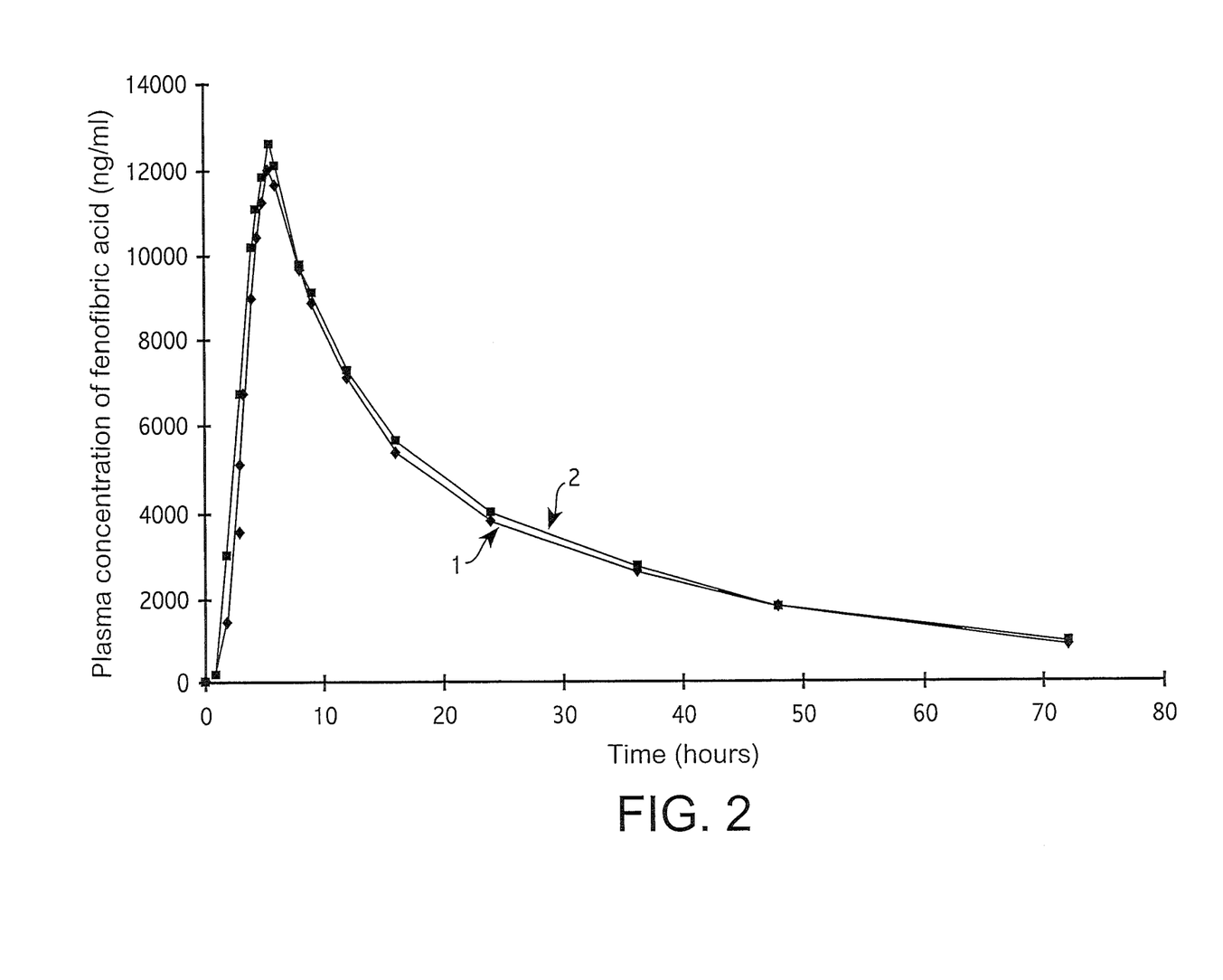
FIG. 2 represents the in vivo release profile of the formulation of example 1C and of a formulation of the prior art in individuals in fed condition. (Curve 1: Lipanthyl® 200M; Curve 2: composition according to the present invention).

The results obtained for Lipanthyl 200 M and for the product of example 1C are represented on FIG. 2 by curves 1 and 2, respectively.

These results show that the composition according to the present invention is bioequivalent to that of Lipanthyl 200 M in individuals in fed condition.

Comparison of the Pharmacokinetic in Individuals Under Fed Condition Versus the Pharmacokinetic in Fasting Individuals Under fasted conditions it was unexpectedly found that the formulation of the invention provided a statically significant increased relative bioavailability of approximately 1.4 times that of the Lipanthyl® as evidenced by a 100% higher mean maximum concentration ($C_{max}$) of the drug and approximately 62% higher mean AUC's. This significant difference between the two formulations disappeared under fed condition.

When the bioavailability of the Lipanthyl® under fed versus fasted conditions was compared, the $C_{max}$ significantly increased (418%) and the mean AUC's significantly increased by (152%).

In contrast, when the bioavailability of the formulation of this invention under fed versus fasted conditions was compared, the Cmax significantly increased by Only 170% and the mean AUC'S were increased only by 76%.

The formulation according to the invention provides a pharmacokinetic profile in which the effect of ingestion of food on the uptake of the drug is substantially reduced over that observed with Lipanthyl®.

Comparative Example 2

Batch ZEF 001

This example illustrates the prior art.

It combines micronization of fenofibrate and the use of a surfactant. It differs from the present invention by the use of the mixture of binding excipients consisting of a cellulose derivative other than HPMC: Avicel PH 101 and polyvinylpyrrolidone (PVP K30).

It is prepared by extrusion-spheronization.

Theoretical formula

| Products | Theoretical amount % |
|---|---|
| Micronized fenofibrate | 75.08 |
| Montanox 80 ® | 4.72 |
| Avicel PH 101 ® | 5.02 |
| PVP K 30 ® | 4.12 |
| Explotab ® | 11.06 |

In vitro dissolution profile

The in vitro dissolution is determined according to a continuous flow cell method with a flow rate of 8 ml/min of sodium lauryl sulfate at 0.1 N. The comparative results with Lipanthyl 200 M are given in 10 the following table.

| | Time (min) | |
|---|---|---|
| | 15 | 30 |
| Example 2 (% dissolved) | 24 | 40 |
| Lipanthyl 200M (% dissolved) | 47.3 | 64.7 |

The dissolution is slower than that observed for Lipanthyl 200 M.

Pharmacokinetic Study Carried Out in Fasting Individuals

The in vivo release profile of the gelatin capsules containing the ZEF 001 granules at doses of 200 mg of fenofibrate is compared with that of the gelatin capsules marketed under the trademark Lipanthyl 200 M.

This study is carried out in 5 fasting individuals receiving a single dose. Blood samples are taken at regular time intervals and fenofibric acid is assayed.

The results are given in the following table and FIG. 3.

| Pharmacokinetic Parameters | Lipanthyl 200M | Example 2 |
|---|---|---|
| $AUC_{o-t}$ (µg · h/ml) | 92 | 47 |
| $AUC_{inf}$ (µg · h/ml) | 104 | 53 |
| $C_{max}$ (µg/ml) | 3.5 | 1.7 |
| $T_{max}$ (hours) | 5.6 | 4.6 |
| Ke (1/hour) | 0.04 | 0.038 |
| Elim ½ (hours) | 18.9 | 20.3 |

Figure 3:
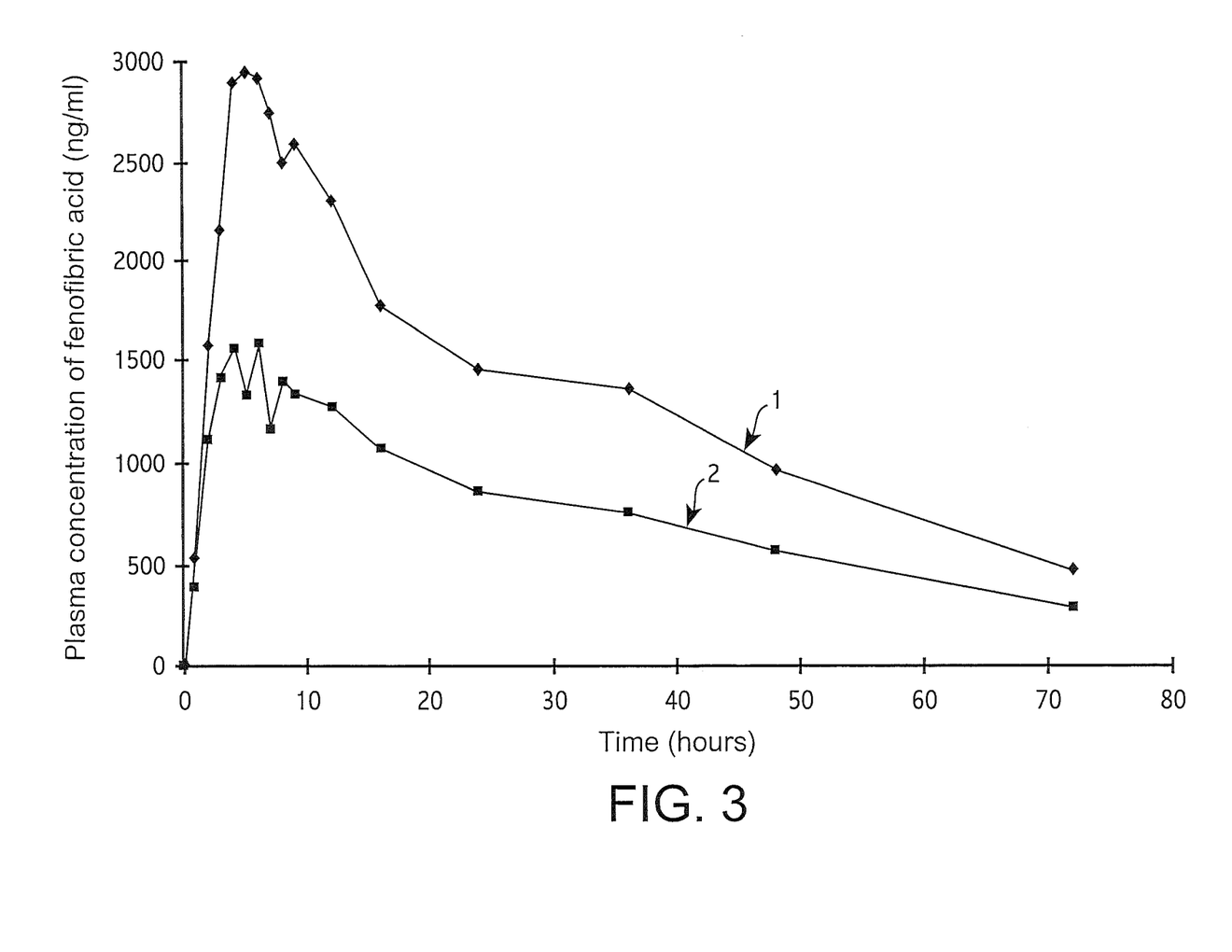
FIG. 3 represents the in vivo release profile of the formulation of comparative example 2 and of a formulation of the prior art in individuals in fed condition.

The results obtained for Lipanthyl 200 M and for the product of example 2 are represented on FIG. 3 by curves 1 and 2, respectively.

These results show the greater bioavailability of Lipanthyl 200 M compared with this formulation based on the prior art.

Example 2 shows that combining the knowledge of the prior art (namely micronization or use of surfactants) does not make it possible to obtain rapid dissolution of fenofibrate. This results in low bioavailability compared with Lipanthyl 200 M.

The compositions prepared according to the present invention show more rapid dissolution than the formula of the prior art and improved bioavailability.

Example 3

Microgranules Coated with an Outer Layer

Microgranules were prepared by spraying an aqueous suspension onto neutral cores.

The composition of the suspension is given in the following table:

| Suspension | Amount (percentage by mass) |
| --- | --- |
| Purified water | 78.09 |
| 35% dimethicone emulsion | 0.19 |
| 30% simethicone emulsion | 0.03 |
| HydroxyPropylMethylCellulose (HPMC) 2910 (Pharmacoat ® 603) | 3.31 |
| Sodium lauryl sulphate | 0.89 |
| Micronized fenofibrate | 17.49 |
| Total | 100.00 |

The composition of the obtained microgranule is given in the following table:

| Formula of microgranules | Amount (kg) |
| --- | --- |
| Micronized fenofibrate | 372.00 |
| Sugar spheres | 96.00 |
| HydroxyPropylMethylCellulose (HPMC) 2910 (Pharmacoat ® 603) | 70.32 |
| Sodium lauryl sulphate | 18.96 |
| 35% dimethicone emulsion | 4.12 |
| 30% simethicone emulsion | 0.67 |
| Talc | 2.72 |
| Purified water | 1660.80 |

Different additional outer layers composed of a suspension of HPMC and talc (2:1, w:w) were applied on the obtained microgranules. They differ from each other:
  by the type of HPMC used: Pharmacoat® 603, 606 or 615. The major difference between these HPMC is their viscosity which increases in the order HPMC 603 <HPMC 606<HPMC 615.
  by the amount of the (HPMC/Talc) suspension applied on the microgranules: 1, 2, 3, 4, 5 or 10%, expressed as dry HPMC/talc relative to the total microgranule.

Dissolution tests were performed with hand-filled gelatine capsules. The mass of microgranules introduced in the capsule was calculated according to the theoretical content of fenofibrate in the formula.

The equipment was composed of:
  a dissolutest (for example: SOTAX AT7 type),
  a pump which allows direct sample analysis,
  a UV spectrophotometer (for example: Lambda 12 from Perkin Elmer).

The dissolution method used was a rotating blade method at 75 rpm according to the European Pharmacopoeia.

The dissolution medium was composed of water with 0.025 M sodium lauryl sulfate. The temperature was set at 37.0° C.±0.5° C.

Dissolution profile as a function of the amount of the (HPMC/Talc) suspension applied on the microgranules The effect exerted on the dissolution profile by the amount of the HPMC/Talc suspension applied on the microgranules was studied. The results are summarized on FIGS. 4 to 6 for HPMC 603, 606 and 615 respectively.

Figure 4:
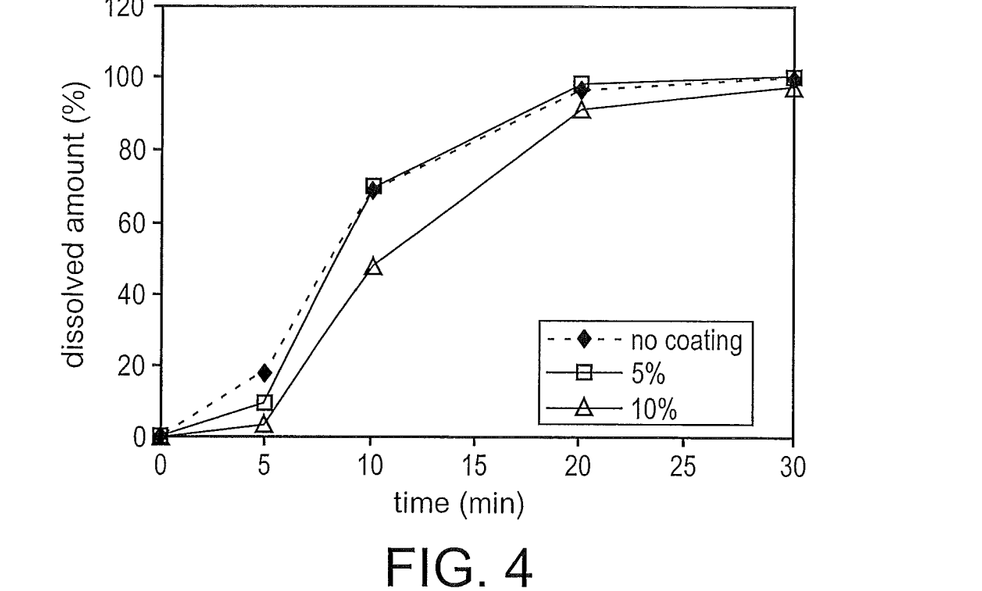
FIG. 4 represents the in vitro dissolution profile as a function of the amount of the (HPMC 603/Talc) suspension applied on the microgranules.
Figure 5:
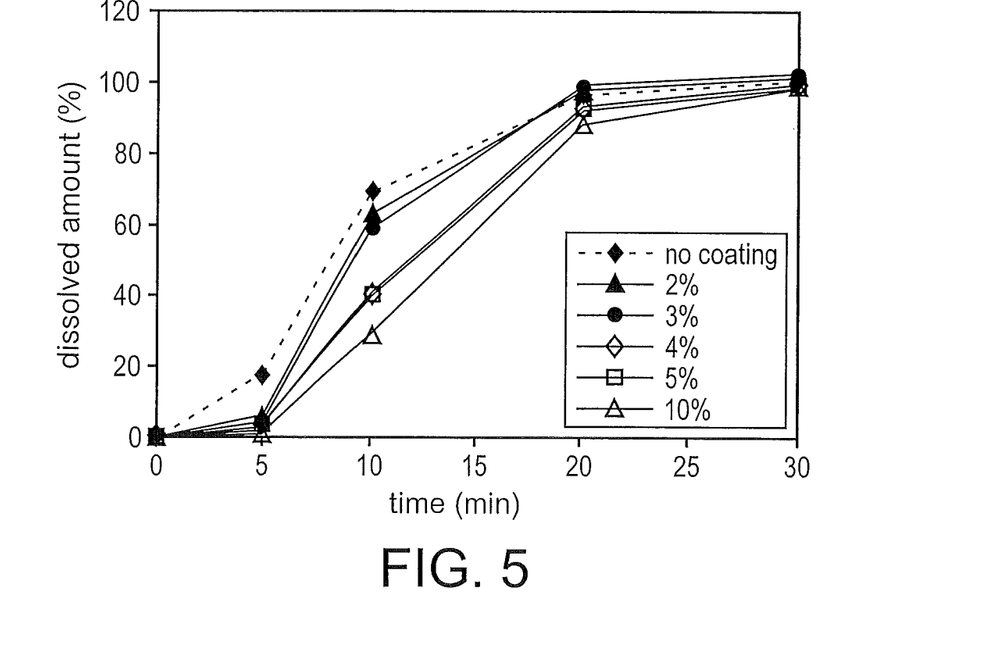
FIG. 5 represents the in vitro dissolution profile as a function of the amount of the (HPMC 606/Talc) suspension applied on the microgranules.
Figure 6:
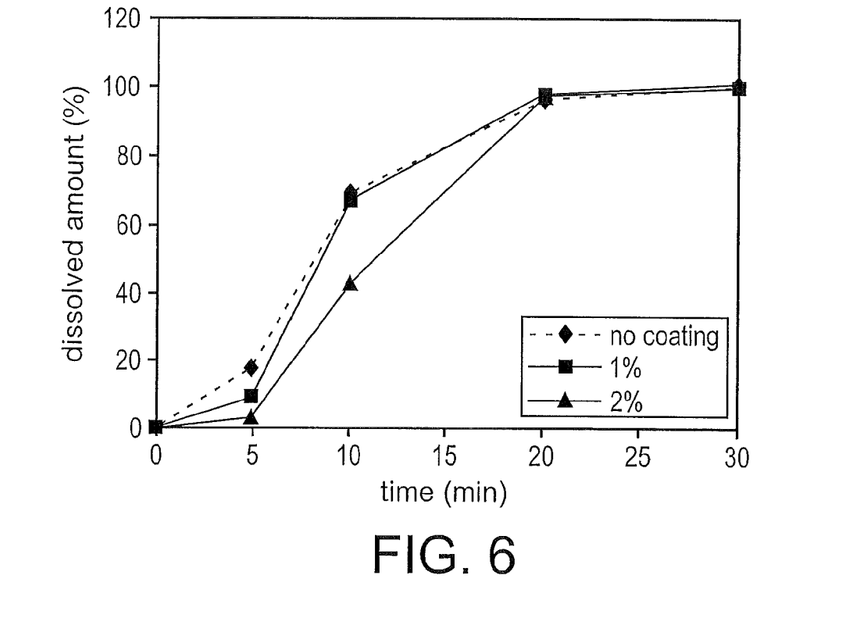
FIG. 6 represents the in vitro dissolution profile as a function of the amount of the (HPMC 615/Talc) suspension applied on the microgranules.

The coating leads to the apparition of a delay after 5 min dissolution.

Example 4

Microgranules Coated with an Outer Layer Applied by Spraying a (HPMC 606/Talc) 4% Suspension Microgranules are obtained by spraying an aqueous suspension of micronized fenofibrate prepared as described in example 3 onto neutral cores, followed by an outer layer of HPMC and talc, the composition of the microgranules is given in the following table:

| FORMULA | PERCENTAGE BY MASS |
| --- | --- |
| Neutral cores | 16.44 |
| Micronized fenofibrate | 63.69 |
| Hydroxypropylmethyl cellulose 3.0 Viscosity cP | 12.04 |
| Sodium lauryl sulfate | 3.25 |
| Dimethicone | 0.25 |
| Simethicone | 0.03 |
| Talc | 0.63 |
| Outer layer | |
| Hydroxypropylmethyl cellulose 6.0 Viscosity cP | 2.57 |
| Talc | 1.1 |

Example 5

Dissolution Profile

A dissolution profile for a fenofibrate composition prepared according to example 4 was carried out by rotating blade method at 75 rpm, according to the European Pharmacopoeia. The dissolution medium was composed of water with 0.025 M sodium lauryl sulfate. The temperature was set at 37° C.±0.5° C.

The vessel was filled with 1000 mL sodium lauryl sulfate 0.025 M. One hand-filled capsules were added to the vessel. The test sample was taken at time intervals of 5 minutes (during 1 hour) and analyzed at a wavelength of 290 nm, through 2 mm quartz cells, against a blank constituted of 0.025 M sodium lauryl sulfate. The results obtained are shown graphically in FIG. 7, on which the percentage of dissolution is shown and in the following table.

Figure 7:
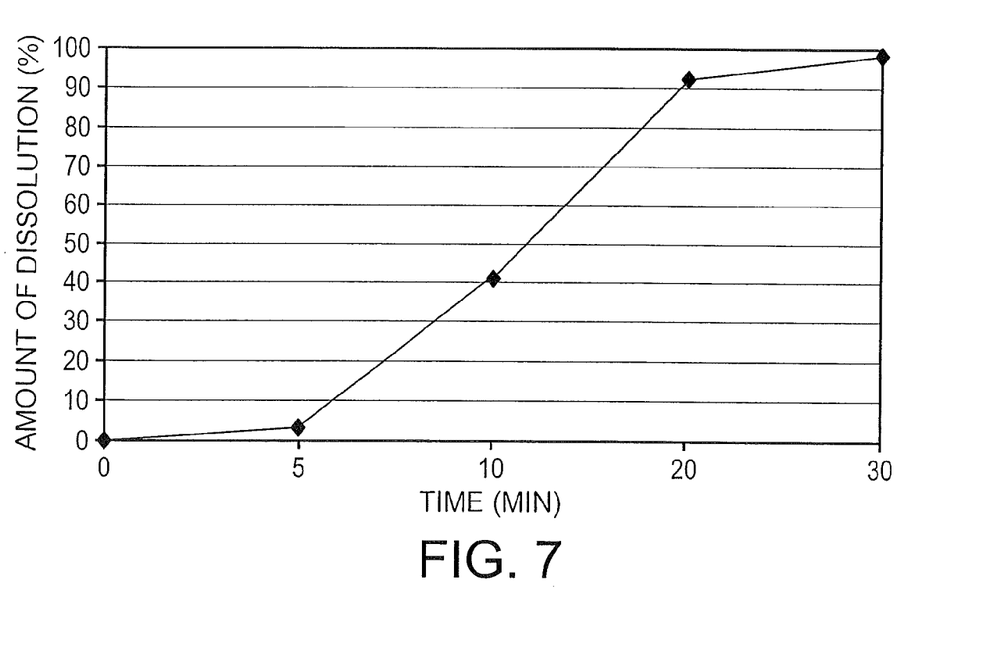
FIG. 7 represents the in vitro dissolution profile as a function of the amount of the (HPMC 606/Talc) 4% suspension applied on the microgranules.

| Time (min) | Amount of dissolution (%) |
| --- | --- |
| 5 | 3 ± 1 |
| 10 | 41 ± 7 |
| 20 | 92 ± 4 |
| 30 | 98 ± 1 |

These results clearly show that the composition according to the invention has a dissolution profile which is less than 10% in five minutes and more than 80% in 20 minutes.

Example 6

A comparison of the relative bioavailability of 130 mg fenofibrate composition prepared according to example 4 and Tricor® 200 mg under fasted conditions and following consumption of a standard high fat FDA test meal in healthy adult subjects.

A test of bioavailability on healthy volunteers was carried out. The following compositions were tested: capsules containing microgranules prepared according to example 4. containing 130 mg of fenofibrate and Tricor® from Abbott Laboratories, containing 200 mg of fenofibrate. The study was carried out on 32 healthy volunteers in a randomized, single-dose, open-label (laboratory blinded), 4-way crossover study to determine the relative bioavailability under fasted and fed conditions in healthy adult subjects. The relative bioavailability of each formulation under fasted and fed conditions was also assessed. Subjects randomized to Treatment A received a single oral dose of 130 mg fenofibrate prepared according to example 4 taken with 240 mL of tap water following a 10-hour fast. Subjects randomized to Treatment B received a single oral dose of the same formulation taken with 240 mL of tap water following a standardized high-fat meal. Subjects randomized to Treatment C received a single oral dose of one Tricor® (fenofibrate) 200 mg micronized capsule taken with 240 mL of tap water following a 10-hour fast. Subjects randomized to Treatment D received a single oral dose of one Tricor® (fenofibrate) 200 mg micronized capsule taken with 240 mL of tap water following a standardized high-fat meal.

In these examples, "fasted" is based on a 10-hour absence of food, however, a skilled artisan would know other methods of preparing fasted conditions. For example, "fasted" may be understood as 10 hour or more absence of food.

The standardized high-fat meal contains approximately 50 percent of total caloric content of the meal from fat or a calorie content of 800-1000 calories of which 50 percent is from fat. An example of the standardized high-fat meal is two eggs fried in butter, two strips of bacon, two slices of toast with butter, four ounces of hash brown potatoes (fired with butter) and eight ounces of whole milk. Substitutions in this test meal can be made as long as the meal provides a similar amount of calories from protein, carbohydrate, and fat and has comparable meal volume and viscosity. The results obtained are given in Tables 1 and 2 below:

TABLE 1

Pharmacokinetic Parameters for Fenofibric Acid Following a Single Dose Under Fasted and Fed (Standard High-Fat FDA Test Meal) Conditions

| Parameter | Treatment A Invention 130 mg (Fasted) | Treatment B Invention 130 mg (Fed) | Treatment C Tricor ® 200 mg (Fasted) | Treatment D Tricor ® 200 mg (Fed) |
| --- | --- | --- | --- | --- |
| $AUC_{0-t}$ (ng · h/mL) | 114853 | 145562 | 109224 | 224330 |
| $AUC_{0-inf}$ (ng · h/mL) | 116134 | 146843 | 111235 | 226004 |
| $C_{max}$ (ng/mL) | 4375 | 9118 | 3413 | 12829 |
| $T_{max}$ (h) | 4.84 | 4.89 | 9.61 | 5.65 |
| $t_{1/2}$ (h) | 19.7 | 18.3 | 21.0 | 19.0 |

TABLE 2

Fed vs Fasted Ratios for Individual Formulations

| Parameter | B: Invention 130 mg (Fed) vs A: Invention 130 mg (Fasted) | D: Tricor ® 200 mg (Fed) vs C: Tricor ® 200 mg (Fasted) |
| --- | --- | --- |
| $AUC_{0-t}$ | 124.8 | 221.1 |
| $AUC_{0-inf}$ | 124.6 | 218.8 |
| $C_{max}$ | 210.2 | 434.2 |

Table 1 shows that the extent of absorption (AUC) of fenofibric acid following administration of 130 mg fenofibrate of the invention is comparable to that of the Tricor® 200 mg capsule under fasted conditions.

In addition, table 2 shows that the maximum plasma concentration ($C_{max}$) for the invention is lower than Tricor®, indicating that food effected the rate of bioavailability for the Tricor® formulation. Specifically, the food effect observed for the invention is approximately 2-fold lower than that observed for the Tricor® 200 mg capsule. This suggests that the rate of bioavailability for the invention is almost independent of the presence of food. In contrast, the rate of bioavailability for Tricor® significantly increased with food.

Example 7

A comparison of the relative bioavailability of 130 mg fenofibrate composition prepared according to in example 4 versus Tricor® 200 mg capsules at steady state in healthy adult subjects on a Therapeutic Lifestyle Change Diet ("TLC").

A test of bioavailability on healthy volunteers was carried out. The following compositions were tested: capsules containing microgranules prepared according to example 4 containing 130 mg of fenofibrate and Tricor® from Abbott Laboratories, containing 200 mg of fenofibrate. The study was carried out on 28 healthy volunteers in a randomized, multiple-dose, open-label (laboratory-blinded), 2-way crossover study to determine and compare the bioavailability of the formulation prepared according to example 4 of the invention relative to Tricor® 200 mg oral capsules immediately following consumption of a TLC diet meal. Subjects randomized to Treatment A received a single oral dose of one 130 mg capsule of the invention taken with 240 mL, of room temperature tap water daily for 7 days. Subjects randomized to Treatment B received a single oral dose of one Tricor® (fenofibrate) 200 mg micronized capsule taken with 240 mL of room temperature tap water daily for 7 days.

The TLC Diet stresses reductions in saturated fat and cholesterol intake. The TLC diet contains approximately 25-30 percent fat per meal. An example of a TLC meals is 1 cup of bran cereal, 1 cup of fat free milk, 8 ounces of orange juice, 1 small banana, 1 slice whole wheat toast, 1 teaspoon of margarine, and coffee, black or with fat free milk. Substitutions in this test meal can be made as long as the meal provides a similar amount of calories from protein, carbohydrate, and fat and has comparable meal volume and viscosity. The results obtained are given in Table 3 below:

TABLE 3

Pharmacokinetic Parameters for Fenofibric Acid Following Multiple Dosing in Healthy Subjects on a TLC Diet

| Parameter | Treatment A Invention 130 mg (Fed) | Treatment B Tricor ® 200 mg (Fed) |
| --- | --- | --- |
| $AUC_{\tau, ss}$ (ng · h/mL) | 182889 | 204988 |
| $C_{max, ss}$ (ng/mL) | 12664 | 13810 |
| $T_{max, ss}$ (h) | 4.896 | 5.343 |
| $C_{av, ss}$ (ng/mL) | 7620 | 8541 |
| $C_{min, ss}$ (ng/mL) | 4859 | 5878 |

The results on table 3 show that the bioavailability of the capsules of the invention and the Tricor® 200 mg capsules are comparable after multiple dosing, immediately following consumption of a TLC diet meal.

Example 8

A Comparison of the Relative Bioavailability of 130 mg fenofibrate composition prepared according to example 4 and Tricor® 200 mg Under Fasted Conditions and Following Consumption of a Therapeutic Lifestyle Change Meal in Healthy Adult Subjects.

A test of bioavailability on healthy volunteers was carried out. The following compositions were tested: capsules containing microgranules prepared according to example 4 containing 130 mg of fenofibrate and Tricor® from Abbott Laboratories, containing 200 mg of fenofibrate. The study was carried out on 32 healthy volunteers in a randomized, single-dose, open-label (laboratory blinded), 4-way crossover study to determine the relative bioavailability of 130 mg of the invention prepared according example 4 to Tricor® 200 mg oral capsules under fasted and fed conditions in healthy adult subjects. The relative bioavailability of each formulation under fasted and fed conditions was also assessed. Subjects randomized to Treatment A received a single oral dose of 130 mg fenofibrate prepared according to example 4 taken with 240 mL tap water under fasted conditions. Subjects randomized to Treatment B received a single oral dose of 130 mg fenofibrate prepared according to example 4 formulation taken with 240 mL of room temperature tap water following a TLC meal. Subjects randomized to Treatment C received a single oral dose of one Tricor® 200 mg capsule taken with 240 mL tap water under fasted conditions. Subjects randomized to Treatment D received a single oral dose of one Tricor® 200 mg capsule taken with 240 mL of tap water following a TLC diet meal.

The results obtained are given in Tables 4 and 5 below:

TABLE 4

Pharmacokinetic Parameters for Fenofibric Acid Following a Single Dose Under Fasted and Fed (Therapeutic Lifestyle Change Meal) Conditions

| Parameter | Treatment A: Invention 130 mg (Fasted) | Treatment B: Invention 130 mg (Fed) | Treatment C: Tricor® 200 mg (Fasted) | Treatment D: Tricor® 200 mg (Fed) |
|---|---|---|---|---|
| $AUC_{0-t}$ (ng·h/mL) | 126031 | 130400 | 123769 | 159932 |
| $AUC_{0-inf}$ (ng·h/mL) | 128020 | 132387 | 129798 | 162332 |
| $C_{max}$ (ng/mL) | 4403 | 7565 | 2734 | 7554 |
| $T_{max}$ (h) | 4.73 | 4.21 | 8.37 | 4.58 |

TABLE 5

Fed vs. Fasted Ratios for Individual Formulations

| Parameter | B: Invention 130 mg (Fed) vs A: Invention 130 mg (Fasted) | D: Tricor® 200 mg (Fed) vs C: Tricor® 200 mg (Fasted) |
|---|---|---|
| $AUC_{0-t}$ | 104.0 | 131.4 |
| $AUC_{0-inf}$ | 103.9 | 127.9 |
| $C_{max}$ | 175.1 | 279.7 |

The results on Table 4 show that following the consumption of a TLC meal, the maximum plasma concentration ($C_{max}$) of fenofibric acid and the extent of absorption (AUC) of the invention is comparable to Tricor®. Similarly, under fasted conditions, the extent of absorption (AUC) of the invention is comparable to Tricor®. But, the maximum plasma concentration ($C_{max}$) of fenofibric acid is greater for the invention than for the Tricor® formulation indicating that the invention is more easily absorbed.

Also, the results on Table 5 show that the consumption of a TLC meal effected the maximum plasma concentration ($C_{max}$) for both the invention and Tricor®. But the food effect is more than 2-fold lower for the invention as compared to Tricor®. This indicates that the rate of bioavailability for the invention is almost independent of the presence of food. In contrast, the rate of bioavailability for Tricor® significantly increased with food.

The invention claimed is:

1. A pharmaceutical composition in the form of granules comprising:
   (a) a neutral core;
   (b) an active layer surrounding the neutral core; and
   (c) a hydrosoluble layer surrounding the active layer;
   wherein said active layer comprises fenofibrate, a surfactant and a binding cellulose derivative;
   and wherein the fenofibrate has a mean particle size of less than about 15 microns.

2. The pharmaceutical composition of claim 1, wherein the mean particle size of the fenofibrate is from 6.2 microns to 7.6 microns.

3. The pharmaceutical composition of claim 1, wherein the dose of fenofibrate is about 50 mg to about 300 mg.

4. The pharmaceuticl composition of claim 1, wherein the dose of fenofibrate is from about 130 mg to about 200 mg.

5. The pharmaceutical composition of claim 1, wherein the dose of fenofibrate is 130 mg.

6. The pharmaceutical composition of claim 1, wherein the binding cellulose derivative is hydroxypropylmethyl cellulose.

7. The pharmaceutical composition of claim 6, wherein said hydroxypropylmethyl cellulose is present in an amount from about 2% by weight to about 20% by weight based on the combined weight of the neutral core and the active layer.

8. The pharmaceutical composition of claim 7, wherein said hydroxypropyirnethyl cellulose has an apparent viscosity of between about 2.4 cP and about 18 cP.

9. The pharmaceutical composition of claim 1, wherein the surfactant is selected from the group consisting of sodium lauryl sulfate, polyoxyethylene 20 sorbitan monooleate, sorbitan monolaurate, polyoxyethyiene sorbitan monolaurate, and sucrose stearate.

10. The pharmaceutical composition of claim 9, wherein said surfactant is present in an amount from about 1% by weight to about 10% by weight relative to the weight of fenofibrate.

11. The pharmaceutical composition of claim 1, wherein said outer hydrosoluble layer comprises a hydrosoluble binder selected from the group consisting of hydroxypropylmethyl cellulose, hydroxypropylcellulose, hydroxyethylcellulose, polyvinylpyrrolidone, and mixtures thereof.

12. The pharmaceutical composition of claim 11, wherein the hydrosoluble binder is hydroxypropylmethyl cellulose.

13. The pharmaceutical composition of claim 12, wherein said hydroxypropylmethyl cellulose in said outer hydrosoluble layer has an apparent viscosity of between about 3 cP and about 15 cP.

14. The pharmaceutical composition of claim 11, wherein said outer hydrosoluble layer further comprises at least one excipient.

15. The pharmaceutical composition of claim 14, wherein said excipient is a lubricant.

16. The pharmaceutical composition of claim 15, wherein said lubricant is talc present in an amount from about 1% by weight to about 10% by weight based on the total weight of the composition.

17. The pharmaceutical composition of claim 14, wherein said excipient is selected from the group consisting of lactose, α-(trimethylsilyl)-ω-methylpoly[oxy(dimethylsilylene)], a mixture of α-(trimethylsilyl)-ω-methylpoly[oxy(dimethylsilylene)] with silicon dioxide, colloidal silicon dioxide, and talc.

18. The pharmaceutical composition of claim 17, wherein the mass ratio of said hydrosoluble binder to talc is from about 1/1 to about 5/1.

19. The pharmaceutical composition of claim 1, wherein said outer hydrosoluble layer is present in an amount from about 1% by weight to about 15% by weight based on the total weight of the composition.

20. The pharmaceutical composition of claim 1, wherein said outer hydrosoluble layer is present in an amount from about 2% by weight to about 4% by weight based on the total weight of the composition.

21. The pharmaceutical pharaceutcal composition of claim 1 wherein the neutral core comprises, sugar, the binding cellulose derivative and the hyclrosoluble layer comprise hydroxypropylmethyl cellulose, the surfactant is sodium lauryl sulfate, and the formulation further comprises dimethicone simethirone and talc.

22. The pharmaceutical composition as in claim 1, wherein said composition is contained in a capsule.

23. The pharmaceutical composition as in claim 1, wherein the granules are in tablet form.

24. The pharmaceutical composition of claim 1, wherein the fenofibric acid $C_{max}$ achieved when administered to a fed human patient is no more than about 100% greater than the fenofibric acid $C_{max}$ achieved when administered to a fasted human patient.

25. The pharmaceutical composition of claim 24, wherein the unit dose of fenofibrate is about 100 mg to about 200 mg.

26. The pharmaceutical composition of claim 24, wherein the unit dose of fenofibrate is about 120 mg to about 150 mg.

27. The pharmaceutical composition of claim 24, compounded in unit dosage form in a gelatin capsule, and wherein the neutral core comprises sugar, the binding cellulose derivative and hydrosoluble layer comprise hydroxypropylmethyl cellulose, the surfactant is sodium lauryi sulfate, and the formulation further comprises dimethicone, simethicone and talc.

28. The pharmaceutical composition of claim 1, wherein the fenofibric acid $C_{max}$ achieved when administered to a fed human patient is no more than about 75% greater than the fenofibric acid $C_{max}$ achieved when administered to a fasted human patient.

29. The pharmaceutical composition of claim 1, wherein the fenofibric acid $T_{max}$ achieved when administered to a fed human patient is about 5 hours, or less, and wherein the fenofibric acid $T_{max}$ achieved when administered to a fasted human patient is about 5 hours, or less.

30. A pharmaceutical composition in unit dose form comprising granules of:
(a) a neutral core;
(b) an active layer surroundng the neutral core; and
(c) a hydrosoluble layer surrounding the active layer;
wherein said active layer comprises; fenofibrate of mean particle size less than about 15 microns, a surfactant, and a binding cellulose derivative; and about 50 mg to about 300 mg of said fenofibrate per unit dose.

31. A pharmaceutical composition in the form of granules comprising:
(a) a neutral core;
(b) an active layer surrounding the neutral core; and
(c) a hydrosoluble layer surrounding the active layer;
wherein said active layer comprises micronized fenofibrate, a surfactant and a binding cellulose derivative; and wherein the binding cellulose derivative is selected from the group consisting of hydroxypropyimethyl cellulose, hydroxyethylmethyl cellulose, microcrystalline cellulose, silicified microcrystalline cellulose, cellulose acetate, methylcellulose, hydroxyethylcelluiose, and hydroxypropylcellulose.

32. The pharmaceutical composition of claim 31, wherein the fenofibric acid $AUC_{inf}$ achieved when administered to a fed human patient is no more than about 25% greater than the fenofibric acid $AUC_{inf}$ achieved when administered to a fasted human patient.

33. A pharmaceutical composition in the form of granules comprising:
an active layer and hydrosoluble layer surrounding said active layer, wherein said active layer comprises micronized fenofibrate, a surfactant and a binding cellulose derivative; and wherein the binding cellulose derivative is selected from the group consisting of hydroxypropylmethyl cellulose, hydroxyethylmethyl cellulose, microcrystalline cellulose, silicified microcrystalline cellulose, cellulose acetate, rnethylceilulose, hyclroxyethylcellulose, and hydroxypropylcellulose.

34. The pharmaceutical composition of claim 33, wherein the fenofibric acid $C_{max}$ and $AUC_{inf}$ achieved when administered to a fed human patient are no more than about 100% greater and about 25% greater than the fenofibric acid $C_{max}$ and $AUC_{inf}$ achieved when administered to a fasted human patient, respectively, and wherein the fenofibric acid $T_{max}$ achieved when administered to a fed or fasted human patient is from about 4 hours to about 5 hours.

* * * * *